United States Patent
Zhang et al.

(10) Patent No.: US 11,560,348 B2
(45) Date of Patent: Jan. 24, 2023

(54) PROCESS FOR THE HYDROFORMYLATION OF OLEFINS USING A COBALT PRE-CATALYST

(71) Applicant: Evonik Operations GmbH, Essen (DE)

(72) Inventors: Baoxin Zhang, Rostock (DE); Christoph Kubis, Nienhagen (DE); Armin Börner, Rostock (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/824,672

(22) Filed: May 25, 2022

(65) Prior Publication Data
US 2022/0402847 A1 Dec. 22, 2022

(30) Foreign Application Priority Data
Jun. 2, 2021 (EP) ..................................... 21177380

(51) Int. Cl.
*C07C 45/50* (2006.01)

(52) U.S. Cl.
CPC .................................. *C07C 45/505* (2013.01)

(58) Field of Classification Search
CPC .................................................... C07C 45/505
See application file for complete search history.

(56) References Cited

U.S. PATENT DOCUMENTS

2021/0032185 A1  2/2021  Roos et al.

OTHER PUBLICATIONS

European Search Report dated Nov. 22, 2021 for European Patent Application No. 21177380.9 (6 pages in German with English machine translation).
Hood, D. M et al. Highly active cationic cobalt (II) hydroformylation catalysts. Science. 2020, vol. 367, pp. 542-548.

*Primary Examiner* — Sikarl A Witherspoon
(74) *Attorney, Agent, or Firm* — Smith, Gambrell & Russell, LLP

(57) ABSTRACT

Process for the hydroformylation of olefins using a cobalt pre-catalyst.

9 Claims, No Drawings

PROCESS FOR THE HYDROFORMYLATION OF OLEFINS USING A COBALT PRE-CATALYST

The invention relates to a process for the hydroformylation of olefins using a cobalt pre-catalyst.

The technical problem on which the present invention was based is that of providing a process with which olefins can be hydroformylated. An increased yield should be achieved in the process.

This object is achieved by a process according to claim 1.

Process comprising the process steps of:
a) adding an olefin;
b) adding a cobalt pre-catalyst,
   wherein the cobalt pre-catalyst is $[Co(acac)(C_4H_8O_2)_4]^+$ $[BF_4]^-$;
c) feeding in synthesis gas;
d) heating the reaction mixture from a) to c), with conversion of the olefin to an aldehyde.

In this process, process steps a), b) and c) can be effected in any desired sequence.

In one variant of the process, the olefin is selected from: ethene, propene, 1-butene, cis-2-butene, trans-2-butene, mixture of cis- and trans-2-butene, raffinate 1, raffinate 2, isobutene, 1-pentene, 2-pentene, 2-methyl-1-butene, 2-methyl-2-butene, 1-methylcyclohexene, tetramethylethene, 1-octene, 2-octenes, cyclooctene, di-n-butene, diisobutene, undecenes, dodecenes, triisobutene, tri-n-butene.

In one variant of the process, the olefin is selected from: 1-butene, cis-2-butene, trans-2-butene, isobutene, 1-pentene, 2-pentene, 1-octene, 2-octenes, di-n-butene, diisobutene, triisobutene, tri-n-butene.

In one variant of the process, the cobalt pre-catalyst is initially charged as a solution.

In one variant of the process, the olefin is added to the initially charged cobalt pre-catalyst solution.

In one variant of the process, synthesis gas is fed in in process step c) at a pressure in the range from 1 to 8 MPa (10 to 80 bar).

In one variant of the process, synthesis gas is fed in in process step c) at a pressure in the range from 4 to 6 MPa (40 to 60 bar).

In one variant of the process, the reaction mixture is heated in process step d) to a temperature in the range from 80° C. to 180° C.

In one variant of the process, the reaction mixture is heated in process step d) to a temperature in the range from 120° C. to 160° C.

The invention is to be illustrated in detail hereinafter by a working example.

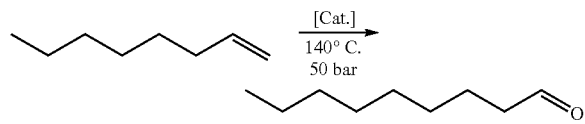

A solution of the pre-catalyst (40.1 mL) is added to a 300 mL Premex autoclave equipped with sparging stirrer, and is charged with synthesis gas to 35 bar. The solution is heated up to 160° C. and the pressure is regulated to 50 bar. After 30 minutes, the temperature is lowered to 140° C. The olefin (1-octene) is now added to the catalyst solution by means of a syringe pump, and the reaction solution is stirred at 50 bar at 140° C. for 3 hours. The reaction mixture is then cooled to room temperature and the pressure is released. The yield is determined by gas chromatography.

The reaction was carried out using three different pre-catalysts.

Pre-catalysts (1) and (2) are comparative pre-catalysts.

Pre-catalysts:
(1) $Co_2(CO)_8$
(2) $Co(acac)_2$
(3) $[Co(acac)(C_4H_8O_2)_4]^+[BF_4]^-$ Reaction Conditions:
T=140° C., p(synthesis gas)=50 bar, t=3 h, olefin=1-octene The experimental results are listed in the following Table:

| Pre-catalyst | Olefin | [Co] (mM) | T (° C.) | t (h) | Yield (%) |
|---|---|---|---|---|---|
| (1) | 1-Octene | 1 | 140 | 3 | 62.7 |
| (2) | 1-Octene | 1 | 140 | 3 | 66.9 |
| (3)* | 1-Octene | 1 | 140 | 3 | 69.3 |

*process according to the invention

In the process according to the invention using pre-catalyst (3), a better yield was achieved than in the two comparative experiments.

As the working example shows, the object is achieved by the process according to the invention.

The invention claimed is:

1. Process comprising the process steps of:
   a) adding an olefin;
   b) adding a cobalt pre-catalyst,
      wherein the cobalt pre-catalyst is $[Co(acac)(C_4H_8O_2)_4]^+[BF_4]^-$;
   c) feeding in synthesis gas;
   d) heating the reaction mixture from a) to c), with conversion of the olefin to an aldehyde.

2. Process according to claim 1, wherein the olefin is selected from:
   ethene, propene, 1-butene, cis-2-butene, trans-2-butene, mixture of cis- and trans-2-butene, raffinate 1, raffinate 2, isobutene, 1-pentene, 2-pentene, 2-methyl-1-butene, 2-methyl-2-butene, 1-methylcyclohexene, tetramethylethene, 1-octene, 2-octenes, cyclooctene, di-n-butene, diisobutene, undecenes, dodecenes, triisobutene, tri-n-butene.

3. Process according to claim 1, wherein the olefin is selected from:
   1-butene, cis-2-butene, trans-2-butene, isobutene, 1-pentene, 2-pentene, 1-octene, 2-octenes, di-n-butene, diisobutene, triisobutene, tri-n-butene.

4. Process according to claim 1, wherein the Co pre-catalyst is initially charged as a solution.

5. Process according to claim 4, wherein the olefin is added to the initially charged Co pre-catalyst solution.

6. Process according to claim 1, wherein synthesis gas is fed in in process step c) at a pressure in the range from 1 to 8 MPa (10 to 80 bar).

7. Process according to claim 1, wherein synthesis gas is fed in in process step c) at a pressure in the range from 4 to 6 MPa (40 to 60 bar).

8. Process according to claim 1, wherein the reaction mixture is heated in process step d) to a temperature in the range from 80° C. to 180° C.

9. Process according to claim 1, wherein the reaction mixture is heated in process step d) to a temperature in the range from 120° C. to 160° C.

* * * * *